United States Patent [19]

Carlson et al.

[11] Patent Number: 5,666,762
[45] Date of Patent: Sep. 16, 1997

[54] RESPIRATION-LIMITED MANUFACTURED SEED

[75] Inventors: William C. Carlson, Olympia; Michael K. McKinnis, Chehalis; Jeffrey E. Hartle, Federal Way, all of Wash.

[73] Assignee: Weyerhaeuser Company, Tacoma, Wash.

[21] Appl. No.: 487,600

[22] Filed: Jun. 7, 1995

Related U.S. Application Data

[63] Continuation-in-part of Ser. No. 781,773, Oct. 23, 1991, Pat. No. 5,427,593, which is a continuation-in-part of Ser. No. 604,656, Oct. 26, 1990, Pat. No. 5,236,469.

[51] Int. Cl.$^6$ .............................. A01C 1/06; A01H 1/00; A01H 5/00
[52] U.S. Cl. ..................... 47/57.6; 47/58; 47/DIG. 9; 47/DIG. 11; 800/200
[58] Field of Search ................... 47/57.6, 58, DIG. 9, 47/DIG. 11; 435/240.1, 240.4, 240.54; 800/200

[56] References Cited

U.S. PATENT DOCUMENTS

| | | | |
|---|---|---|---|
| 3,545,129 | 12/1970 | Schreiber et al. | 47/57.6 |
| 3,688,437 | 9/1972 | Hamrin | 47/57.6 |
| 3,734,987 | 5/1973 | Hamrin | 264/54 |
| 3,850,753 | 11/1974 | Chibata et al. | 195/109 |
| 4,166,006 | 8/1979 | Hertl et al. | 435/244 |
| 4,252,827 | 2/1981 | Yokoyama et al. | 424/366 |
| 4,465,017 | 8/1984 | Simmons | 118/418 |
| 4,562,663 | 1/1986 | Redenbaugh | 47/58 |
| 4,583,320 | 4/1986 | Redenbaugh | 47/57.6 |
| 4,615,141 | 10/1986 | Janick et al. | 47/57.6 |
| 4,665,648 | 5/1987 | Branco et al. | 47/57.6 |
| 4,715,143 | 12/1987 | Redenbaugh et al. | 47/57.6 |
| 4,769,945 | 9/1988 | Motoyama et al. | 47/57.6 |
| 4,777,762 | 10/1988 | Redenbaugh et al. | 47/57.6 |
| 4,779,376 | 10/1988 | Redenbaugh | 47/57.6 |
| 4,780,987 | 11/1988 | Nelson et al. | 47/57.6 |
| 4,802,305 | 2/1989 | Kojimoto et al. | 47/57.6 |
| 4,806,357 | 2/1989 | Garrett et al. | 427/4 |
| 4,808,430 | 2/1989 | Kouno | 427/4 |
| 4,866,096 | 9/1989 | Schweighardt | 514/756 |
| 4,879,839 | 11/1989 | Gago et al. | 47/57.6 |
| 5,010,685 | 4/1991 | Sakamoto et al. | 47/57.6 |
| 5,044,116 | 9/1991 | Gago et al. | 47/57.6 |

FOREIGN PATENT DOCUMENTS

| | | |
|---|---|---|
| 1241552 | 9/1988 | Canada. |
| 1250296 | 2/1989 | Canada. |
| 0 107 141 | 5/1984 | European Pat. Off.. |
| 0 380 692 | 8/1990 | European Pat. Off.. |
| 61-040708 | 2/1986 | Japan. |
| 62-275604 | 11/1987 | Japan. |
| 63-133904 | 6/1988 | Japan. |
| 63-152905 | 6/1988 | Japan. |
| 2-046240 | 2/1990 | Japan. |
| WO91/01803 | 2/1991 | WIPO. |

OTHER PUBLICATIONS

Redenbaugh et al., "Encapsulation of Somatic Embryos in Synthetic Seed Coats," *HortScience* 21 (No. 3, Section 2): 819–820 (1986) (Abstract of presentation at XXII Int'l Hortic. Cong., Aug. 10–18, 1986, Davis, CA).

Redenbaugh et al., "Encapsulation of Somatic Embryos for Artificial Seed Production" (Abstract), In Vitro 20 (Part 2): 256–257 (1984).

Fujii et al., "Improving Plantlet Growth and Vigor from Alfalfa Artificial Seed" (Abstract), In Vitro 24 (No. 3, Part 2):70A (1989).

Fujii et al., "ABA Maturation and Starch Accumulation in Alfalfa Somatic Embryos" (Abstract), In Vitro 25 (No. 3, Part 2): 61A (1989).

Janick, "Production of Synthetic Seed via Desiccation and Encapsulation" (Abstract), In Vitro 24 (No. 3, Part 2):70A (1989).

Kamada et al., "New Methods for Somatic Embryo Induction and Their Use for Synthetic Seed Production" (Abstract), In Vitro 24 (No. 3, Part 2):71A (1988).

Bapat and Rao, "Sandalwood Plantlets from 'Synthetic Seeds,'" *Plant Cell Reports* 7:434–436 (1988).

Datta and Potrykus, "Artificial Seeds in Barley: Encapsulation of Microspore-Derived Embryos," *Theor. Appl. Genet.* 77:820–824 (1989).

Fujii et al., "Artificial Seeds for Plant Propagation," *Trends in Bio/Technol.* 5:335–339 (1987).

Gupta and Durzan, "Biotechnology of Somatic Polyembryogenesis and Plantlet Regeneration in Loblolly Pine," *Bio/Technol.* 5:147–151 (1987).

Ibarbia, "Synthetic Seed: Is It the Future," *Western Grower and Shipper* 59:12 (1988).

Kim and Janick, "ABA and Polyox–Encapsulation or High Humidity Increases Survival of Desiccated Somatic Embryos of Celery," *HortScience* 24:674–676 (1989).

Kitto and Janick, "Production of Synthetic Seeds by Encapsulating Asexual Embryos of Carrot," *J. Amer. Soc. Hort. Sci.* 110:277–282 (1985).

(List continued on next page.)

*Primary Examiner*—David T. Fox
*Assistant Examiner*—Melissa L. Kimball
*Attorney, Agent, or Firm*—Klarkquist, Sparkman, Campbell, Leigh & Whinston LLP

[57] ABSTRACT

The present invention provides manufactured seeds comprising totipotent plant tissue and a hydrated gel, preferably surrounded by a protective seed coat. The cotyledons of the germinating totipotent plant tissue can be enclosed in a shoot restraint that is resistant to penetration by the growing cotyledons. The manufactured seeds can be prepared for long-term storage, e.g., by sparging the hydrated gel with a respiration-limiting gas before, during, or after assembly of the manufactured seed. The seed is then preferably stored in an atmosphere containing levels of a respiration-limiting gas sufficient to keep respiration of the totipotent plant tissue at reduced levels.

18 Claims, 5 Drawing Sheets

OTHER PUBLICATIONS

Kitto and Janick, "A Citrus Embryo Assay to Screen Water–Soluble Resins as Synthetic Seed Coats," *HortScience* 20:98–100 (1985).

Redenbaugh et al., "Encapsulated Plant Embryos", *Advances in Biotechnical Processes* 9:225–248 (1988).

Redenbaugh et al., "Somatic Seeds: Encapsulation of Asexual Plant Embryos," *Bio/Technol.* 4:797–801 (1986).

Redenbaugh et al., "Encapsulation of Somatic Embryos in Synthetic Seed Coats," *HortScience* 22:803–809 (1987).

Redenbaugh et al., "Scale–Up: Artificial Seeds," in Green et al. (eds.), *Plant Tissue and Cell Culture*, pp. 473–493, Alan R. Liss, NY (1987).

Rogers, "Synthetic–Seed Technology," *Newsweek*, Nov. 28, 1983.

Stuart and Redenbaugh, "Use of Somatic Embryogenesis for the Regeneration of Plants," in LeBaron et al. (eds.), *Biotechnology in Agricultural Chemistry*, Ch. 6, pp. 87–96, American Chemical Society, Washington, D.C. (1987).

Teasdale and Buxton, "Culture of *Pinus radiata* Embryos with Reference to Artificial Seed Production," *New Zealand J. For. Sci.* 16:387–391 (1986).

Adlercreutz and Mattiasson, "Oxygen Supply to Immobilized Cells: 1. Oxygen Production by Immobilized *Chlorella pyrenoidosa*," *Enzyme Microbial Technol.* 4:332–336 (1982).

Adlercreutz and Mattiasson, "Oxygen Supply to Immobilized Biocatalysts. A Model Study," *Acta Chem. Scand.* B36:651–653 (1982).

Adlercreutz and Mattiasson, "Oxygen Supply to Immobilized Cells. 3. Oxygen Supply by Hemoglobin or Emulsions of Perfluorochemicals," *Eur. J. Appl. Microbiol. & Biotechnol.* 16:165–170 (1982).

Mattiasson and Adlercreutz, "Use of Perfluorochemicals for Oxygen Supply to Immobilized Cells," *Ann. N.Y. Acad. Sci.* 413:545–547 (1984).

Damiano and Wang, "Novel Use of a Perfluorocarbon for Supplying Oxygen to Aerobic Submerged Cultures," *Biotechnol. Letters* 7:81–86 (1985).

Chandler et al., "Effects of Emulsified Perfluorochemicals on Growth and Ultrastructure of Microbial Cells in Culture," *Biotechnol. Letters* 9:195–200 (1987).

King et al., "Perfluorochemicals and Cell Culture," *Biotechnol.* 7:1037–1042 (1989).

Clark et al., "The Physiology of Synthetic Blood," *J. Thorac. & Cardiovasc. Surg.* 60:757–773 (1970).

Fujita et al., "Fluorocarbon Emulsion as a Candidate for Artificial Blood," *Europ. Surg. Res.* 3:436–453 (1971).

Geyer, "'Bloodless' Rats Through the Use of Artificial Blood Substitutes," *Fed. Proceed.* 34:1499–1505 (1975).

Clark et al., "Emulsions of Perfluoronated Solvents for Intravascular Gas Transport," *Fed. Proceed.* 34:1468–1477 (1975).

Riess and Le Blanc, "Perfluoro Compounds as Blood Substitutes," *Angew. Chem. Int. Ed. Engl.* 17:621–634 (1978).

Davis et al., "Novel Compositions of Emulsified Perfluorocarbons for Biological Applications," *Brit. J. Pharmacol.* 89:665P (1986).

"FLUORINERT™ Electronic Liquids" brochure, 3M Industrial Chemical Products Division, St. Paul, Minnesota (1989).

"'FLUORINERT™ Electronic Liquids' for Direct Contact Dielectric Cooling" brochure, Chemical Products Division, St. Paul, Minnesota (1989).

Bapat et al., "In Vivo Growth of Encapsulated Axillary Buds of Mulberry, (*Morus indica* L.)," *Plant Cell, Tissue and Organ Culture* 20:69–70 (1990).

Li, "Somatic Embryogenesis and Synthetic Seed Technology Using Carrot as a Model System," in *Synseeds: Applications of Synthetic Seeds to Crop Improvement*, Redenbaugh, Ed., CRC Press, Florida (1993), chap. 16.

Sanada et al., "Celery and Lettuce," in *Synseeds: Applications of Synthetic Seeds to Corp Improvement*, Redenbaugh, Ed., CRC Press, Florida (1993), chap. 17.

Bapat, "Studies on Synthetic Seeds of Sandalwood (*Santalum album* L.) and Mulberry (*Morus indica* L.)," in *Synseeds: Applications of Synthetic Seeds to Crop Improvement*, Redenbaugh, Ed., CRC Press, Florida (1993), chap. 21.

Senaratna, "Artificial Seeds," *Biotech. Adv.* 10:379–392 (1992).

Redenbaugh et al., "III.3 Artificial Seeds—Encapsulated Somatic Embryos," *Biotech. in Agr. & For.* 17:395–416 (1991).

*Brown, "An Experimental Study of the Permeability to Gases of the Seed–Coat Membranes of Cucurbita Pepo," *Annals of Botany* 14:379–395 (1940).

*Goodsell et al., "The Effect of Moisture and Temperature During Storage on Cold Test Reaction of *Zea mays* Seed Stored in Air, Carbon Dioxide, or Nitrogen," *Agronomy J.* 47:61–64 (1955).

*Kidd, "The Controlling Influence of Carbon Dioxide in the Maturation, Dormancy, and Germination of Seeds—Part I.," *Royal Society Proceedings* 87:408–421 (1914).

*Kidd, "Influence of Carbon Dioxide in Maturation, etc., of Seeds," *Royal Society Proceedings* 87:609–625 (1914).

*Hoffman, "Breaking Wild Oat Dormancy with Gases at High Pressure," *Weeds* 9:493 (1961).

*Nelson, "Successful Storage of Southern Pine Seed for Seven Years," *J. Forestry* 38:443–444 (1940).

*Andersen, "The Effect of Carbon Dioxide and Some Other Gases in the Germination of Seeds of *Poa compressa*," (Abstract), *Am. J. Botany* 20:678–679 (1933).

*Corbineau et al., "Control of Seed Germination and Dormancy by the Gaseous Environment," in *Seed Development and Germination*, Kigel and Galili, Ed., Marcel Dekker, Inc., New York (1995), chap. 14.

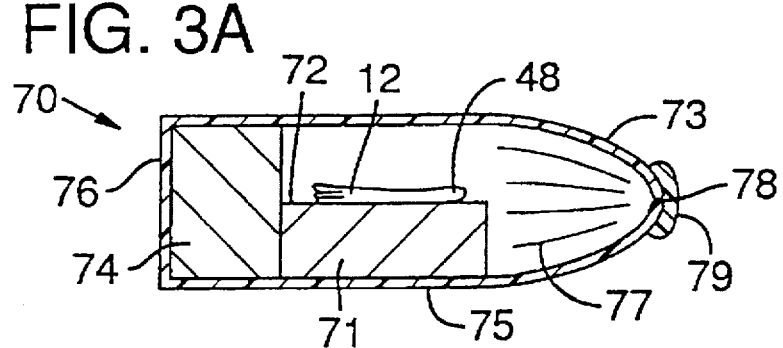
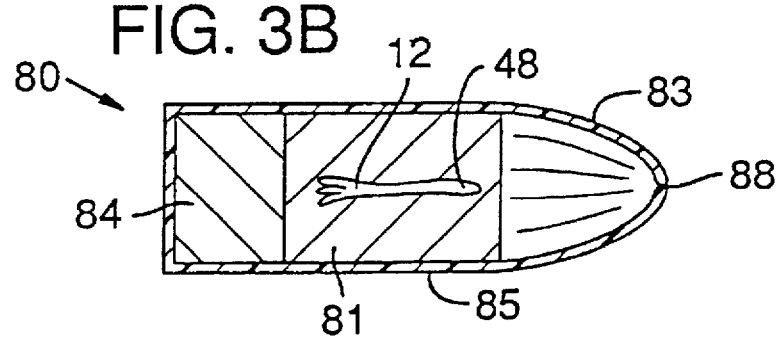
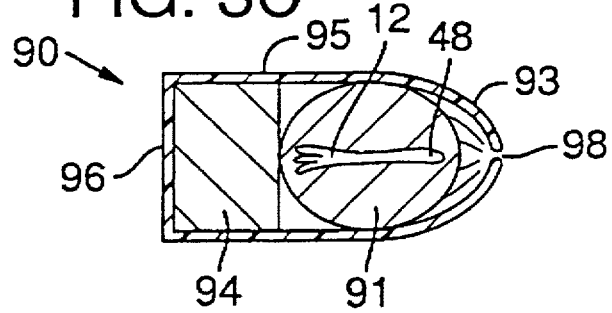
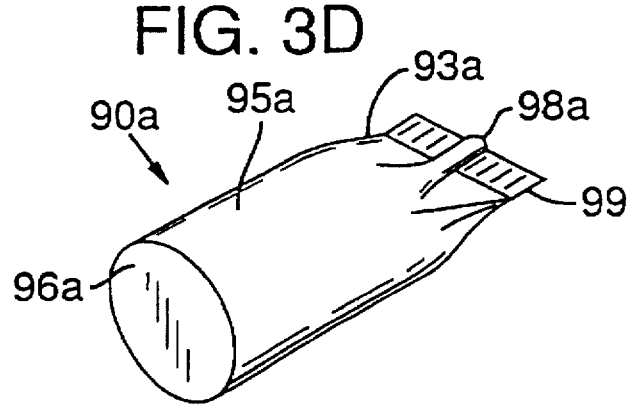

RESPIRATION-LIMITED MANUFACTURED SEED

CROSS REFERENCE TO RELATED APPLICATION

This application is a continuation-in-part of U.S. patent application Ser. No. 07/781,773, filed on Oct. 23, 1991, now U.S. Pat. No. 5,427,593, incorporated herein by reference, which is a continuation-in-part of U.S. patent application Ser. No. 07/604,656, filed on Oct. 26, 1990, now U.S. Pat. No. 5,236,469, also incorporated herein by reference.

FIELD OF THE INVENTION

This invention relates to manufactured seed, each containing a unit of totipotent plant tissue, that can be sown like natural seed and produce viable germinants. This invention also relates to methods for producing such manufactured seed and methods for propagating plants using such manufactured seeds.

BACKGROUND OF THE INVENTION

Modern agriculture, including silviculture, often requires the planting of large numbers of substantially identical plants genetically tailored to grow optimally in a particular locale or to possess certain other desirable traits. Production of new plants by sexual reproduction, which yields botanic seeds, can be slow and is often subject to genetic recombinational events resulting in variable traits in the progeny. Also, such crossing is time- and labor-intensive. Further, inbred strains such as those used to perform such crosses often lack vigor, resulting in low seed productivity.

Despite the drawbacks of conventional crossbreeding by sexual means, botanic seeds produced by such methods have an important advantage in that each seed comprises food-storage organs and protective structures that shelter the plant embryo inside the seed from the harsh soil environment and nurture the embryo during the critical stages of sowing and germination. Without such organs and structures, the plant embryo would be incapable of surviving in nature until it grew to seedling size. Moreover, a botanic seed can survive for long periods of time, often for several years, until conditions are favorable for germination.

In view of the disadvantages of producing large numbers of identical progeny plants by sexual means, propagation of commercially valuable plants via culturing of somatic or zygotic plant embryos has been intensively studied. Such "asexual" propagation has been shown for some species to yield large numbers of genetically identical embryos each having the capacity to develop into a normal plant. Unfortunately, these embryos, which are produced under laboratory conditions, lack the protective and nutritive structures found in botanic seeds. As a result, the embryos must usually be further cultured under laboratory conditions until they reach an autotrophic "seedling" state characterized by an ability to produce their own food via photosynthesis, resist desiccation, produce roots able to penetrate soil, and fend off soil microorganisms. Such extensive laboratory culture during several distinct stages in plant development is time-consuming, resource-intensive, and requires skilled labor.

Some researchers have experimented with the production of "artificial" seeds (i.e., "seed analogs" or, preferably, "manufactured seeds") in which individual plant somatic or zygotic embryos are encapsulated in a hydrated gel. This method evolved from research showing that encapsulating natural seeds in hydrated gels can improve germination in some species.

The hydrated gels used for producing manufactured seeds rapidly lose water to the ambient air or soil on sowing and fail to provide optimal protection to the embryo from mechanical damage resulting from handling and mechanical sowing and from attack by various plant pathogens, herbivores, or other pests, either before or after germination.

In agriculture, natural seed is normally sown during a relatively short period of the biological year. In order to plant large quantities of manufactured seed in this relatively short sowing period, either extremely rapid manufacturing procedures must be developed or the seeds must be stored and thereby accumulated as they are manufactured. It would be possible to develop equipment for manufacturing seed at a speed that would support sowing large crops without long-term seed storage, but seed storage would make the production of manufactured seed more efficient. It is therefore desirable to develop methods that would allow accumulation and long-term storage of manufactured seed. It is also desirable to develop manufactured seeds capable of extended storage without substantial loss of viability before sowing. The present invention meets these and other needs.

SUMMARY OF THE INVENTION

The present invention provides manufactured seeds comprising a plant embryo or other unit of totipotent plant tissue. The totipotent plant tissue is preferably protected from mechanical damage, desiccation, and attack by pathogens, pests, etc. by a manufactured seed coat. In one embodiment of the present invention, the seed coat comprises a gas-impermeable shell defining an opening, across which is preferably disposed a gas-permeable seal.

The totipotent plant tissue is preferably disposed relative to, and preferably surrounded by or in contact with, a hydrated gel so as to allow the transfer of liquid, dissolved solutes, and gases from the gel to the plant tissue. The gel can comprise an inert oxygen-absorbing or oxygen-carrying compound such as a perfluorocarbon or silicone oil. The gel serves as a "synthetic gametophyte" for the totipotent plant tissue in a manner analogous to the gametophyte portion of a natural botanic seed, i.e., the endosperm or other seed nutritive tissue, depending upon the species from which the totipotent plant tissue originates.

The manufactured seed preferably includes some provision for a restraint enclosing at least the shoot end of the totipotent plant tissue. The restraint is resistant to penetration by a growing shoot, preventing the cotyledon(s) and/or other shoot structure of the totipotent plant tissue from growing into and becoming entrapped in the gel, yet permitting access of the plant tissue to gases and liquids. The restraint along with structures attached thereto is adapted to be shed distally off the shoot end during germination of the plant tissue.

Such a manufactured seed can be prepared for long-term storage, for example, if the hydrated gel comprises an amount of a respiration-limiting gas sufficient to substantially reduce respiration of the totipotent plant tissue, including, for example, carbon dioxide or nitrogen. This can be accomplished, for example, by exposing the gel to the respiration-limiting gas before, during, or after assembly of the manufactured seed, i.e., before the totipotent plant tissue is inserted into or otherwise disposed in fluid contact with the gel. It is preferable, after exposure of the gel to the respiration-limiting gas and/or assembly of the manufactured seed to store the manufactured seed in the presence of a concentration of the same or a different respiration-limiting gas to keep respiration of the totipotent plant tissue at reduced levels. Before sowing the manufactured seed, the stored seed can simply be exposed to an oxygen-containing atmosphere such as air or an oxygen-enriched atmosphere so as to provide the totipotent plant tissue with a gas environment that supports germination of the plant tissue, preferably until levels of the respiration-limiting gas inside the seeds drop, and/or levels of molecular oxygen inside the seeds rise, to a level that supports germination.

BRIEF DESCRIPTION OF THE DRAWINGS

FIG. 3A is a cross-sectional view of a manufactured seed usable in a mechanical sowing process.

FIG. 3B is a cross-sectional view of an alternative embodiment of the manufactured seed shown in FIG. 3A.

FIG. 3C is a cross-sectional view of another alternative embodiment to the manufactured seed shown in FIG. 3A.

FIG. 3D is an isometric view of the exterior of an alternative embodiment to that shown in FIG. 3C.

DETAILED DESCRIPTION OF THE INVENTION

Totipotent Plant Tissue

Figure 1A:
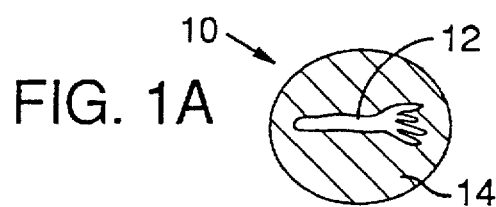
FIG. 1A is a cross-sectional view of a manufactured seed according to the present invention comprising a unit of totipotent plant tissue encapsulated in a hydrated oxygenated gel.

A manufactured seed, according to one aspect of the present invention, comprises a unit of totipotent plant tissue. As used herein, "totipotent" refers to a capacity to grow and develop into a normal plant. Totipotent plant tissue has both the complete genetic information of a plant and the ready capacity to develop into a complete plant if cultured under favorable conditions. As is generally known in the art, totipotent plant tissue is obtainable from any of several areas of a plant, such as meristematic tissue and plant embryonic tissue.

Meristematic tissue is comprised of undifferentiated plant cells that divide to yield other meristematic cells, as well as differentiated cells that elongate and further specialize to form structural tissues and organs of the plant. Meristematic tissue is located, for example, at the extreme tips of growing shoots or roots, in buds, and in the cambium layer of woody plants.

Plant embryonic tissue can be found (in the form of a "zygotic" embryo) inside a botanic seed of the plant produced by sexual reproduction. Also, plant "somatic" embryos can be produced by culturing totipotent plant tissue such as meristematic tissue by standard methods under laboratory conditions in which the cells comprising the tissue are separated from one another and urged to develop into minute complete embryos. Alternatively, a process termed "cleavage polyembryogeny" known in the art can be induced during natural embryo development in seed.

As used herein, a "unit" of totipotent plant tissue is a mass of such tissue that can be individually handled and that can develop into a germinant and ultimately a plant under favorable conditions.

For use in preferred embodiments of manufactured seeds according to the present invention, the unit of totipotent plant tissue preferably is developed sufficiently to have a shoot end and a radicle end. In certain species of plants, the shoot end includes one or more cotyledons in some stage of development. For example, such totipotent plant tissue of gymnosperms usually has multiple cotyledons situated on or near the shoot apex. This is also the case with many dicotyledonous plants. In other types of plants, the cotyledon (s) are situated in locations other than the shoot end.

Hydrated Gels

A "gel" is a substance that is prepared as an aqueous colloidal solution and that will, or can be caused to, form a semisolid material. (As used herein, "hydrated" denotes the presence of free water interspersed throughout the matrix of gel molecules.) Conversion of a liquid gel solution into a semisolid material is termed herein "curing" or "setting" of the hydrated gel. In manufactured seeds according to the present invention, the hydrated gel, along with any other substances included therein, can serve as an "artificial gametophyte" for the totipotent plant tissue.

As can be ascertained from the foregoing, "hydrated" denotes water-containing. Hydrated gels are prepared by first dissolving in water (where water serves as the solvent, or "continuous phase") a hydrophilic polymeric substance (serving as the solute, or "disperse phase") that, upon curing, combines with the continuous phase to form the semisolid material. In other words, the water becomes homogeneously associated with the solute molecules without experiencing any substantial separation of the continuous phase from the disperse phase. However, water molecules can be freely withdrawn from a cured hydrated gel, such as by evaporation or imbibition by germinating plant tissue. When cured, a hydrated gel has the familiar characteristic of a compliant solid, like a mass of gelatin, where the compliance becomes progressively less and the gel becomes more "solid" to the touch as the relative amount of water in the gel is decreased.

In addition to being water-soluble, suitable gel solutes are not cytotoxic and substantially non-phytotoxic. As used herein, a "substantially non-phytotoxic" substance is a substance that does not interfere substantially with normal plant development, such as by killing a substantial number of plant cells, substantially altering cellular differentiation or maturation, causing mutations, disrupting a substantial number of cell membranes or substantially disrupting cellular metabolism, or substantially disrupting some other vital process.

Candidate gel solutes include, but are not limited to, the following: sodium alginate, agar, agarose, amylose, pectin, dextran, gelatin, starch, amylopectin, modified celluloses such as methylcellulose and hydroxyethylcellulose, and polyacrylamide. Other hydrophilic gel solutes can also be used, so long as they possess similar hydration and gelation properties and lack of phytotoxicity. Also, it is important to be able to add, as required, other substances such as plant nutrients, antibiotics, plant growth regulators, or emulsified materials to a gel without substantially interfering with gelling ability.

Hydrated gels are typically prepared by dissolving a gel solute, usually in fine particulate form, in water to form a gel solution. Depending upon the particular gel solute, heating is usually necessary, sometimes to boiling, before the gel solute will dissolve. Subsequent cooling will cause many gel solutions to reversibly "set" or "cure" (become gelled). Certain gels are termed "reversible" because reheating the cured hydrated gel will re-form the gel solution. Other gels typically require a "complexing" agent serving to chemically cure the gel by crosslinking gel solute molecules. For example, sodium alginate is cured by adding calcium nitrate ($Ca(NO_3)_2$) or salts of other divalent ions such as, but not limited to, calcium, barium, lead, copper, strontium, cadmium, zinc, nickel, cobalt, magnesium, and iron to the gel solution. Many of the gel solutes requiring complexing agents are termed "irreversible" because reheating will not re-establish the gel solution.

The concentration of gel solute required to prepare a satisfactory hydrated gel varies depending upon the particular gel solute. For example, a useful concentration of sodium alginate is within a range of about 0.5% w/v to about 2.5% w/v, preferably about 0.9% w/v to 1.5% w/v. A useful concentration of agar is within a range of about 0.8% w/v to about 2.5% w/v, preferably about 1.8% w/v. (As used herein, the "% w/v" concentration unit is equivalent to grams of solute per 100 ml of solvent.) Gel concentrations up to about 24% w/v have been successfully employed for other gels. In general, gels cured by complexing require less gel solute to form a satisfactory gel than "reversible" gels.

It is preferable to provide the totipotent plant tissue with any of various additives, e.g., plant nutrients and other beneficial substances such as vitamins and a source of carbon and energy (herein collectively termed generally "nutrients"), antibiotics, or plant growth regulators. See, e.g., the "adjuvants" listed in U.S. Pat. No. 4,779,376 (Redenbaugh), incorporated herein by reference. The additives can be provided by dissolving the gel solute in a solution of the additives or adding a volume of a concentrated solution (or suspension, etc.) of the additive to the gel solution before curing the gel. An additive also can be added to a gel by placing a cured hydrated gel, lacking the additive, in contact with an additive solution, upon which additive molecules pass into the hydrated gel as a result of the concentration gradient from the solution to the interior of the gel mass. Although the hydrated gel unit preferably contains nutrients dissolved therein, it is possible to dissolve the additive in a separate additive-containing unit in contact with the gel unit. For example, the hydrated-gel mass lacking the additive is placed in contact with a second mass of the same or a different type of hydrated gel containing the additive. As a result of a concentration gradient of the additive between the two hydrated gel masses, the additive will migrate from the additive-containing gel mass to the gel mass originally lacking the additive.

Yet another way to provide a hydrated gel with an additive is to place a gel mass lacking the additive in contact with a hydrated gel mass comprising the additive in microencapsulated form or the additive associated with any substantially non-phytotoxic substance that will allow the additive dissolved or suspended therein to be bulk-transferred, e.g., via water convection, to the first gel mass. Representative substances include, but are not limited to, water, a second hydrated gel similar to the first hydrated gel, vermiculite, perlite, or any polymeric material that is non-phytotoxic and that can release the additive over time.

A number of appropriate nutrient formulations exist in the art, including a number of proprietary formulations. For example, a popular medium is the "MS liquid" (Murashige and Skoog, *Physiologia Plantatum* 15:473–497 (1962)) containing the following dissolved in water:

| | |
|---|---|
| $NH_4NO_3$ | 1650 mg/L |
| $KNO_3$ | 1900 mg/L |
| $CaCl_2.2H_2O$ | 440 mg/L |
| $MgSO_4.7H_2O$ | 370 mg/L |
| $KH_2PO_4$ | 170 mg/L |
| $Na_2EDTA$ | 37.25 mg/L |
| $FeSO_4.7H_2O$ | 27.85 mg/L |
| $MnSO_4.4H_2O$ | 22.3 mg/L |
| $ZnSO_4.4H_2O$ | 8.6 mg/L |
| $H_3BO_3$ | 6.2 mg/L |
| KI | 0.83 mg/L |
| $Na_2MoO_4.2H_2O$ | 0.25 mg/L |
| $CuSO_4.5H_2O$ | 0.025 mg/L |
| $CoCl_2.6H_2O$ | 0.025 mg/L |
| Glycine | 0.2 mg/100 $cm^3$ |
| Nicotinic Acid | 0.05 mg/100 $cm^3$ |
| Pyridoxine.HCl | 0.05 mg/100 $cm^3$ |
| Thiamine.HCl | 0.01 mg/100 $cm^3$ |
| Kinetin | 0.1 mg/L |
| Myoinositol | 100 mg/L |
| IAA | 10 mg/L |
| Sucrose | 30000 mg/L |
| pH | 5.7–5.8 |

(Note: An "MS medium" will also contain 1.0% w/v agar. Murashige and Skoog, id.) Of course, when adding a nutrient solution to a gel solution, the concentrations of both solutions should be high enough such that the resulting mixture of the two solutions has the proper concentrations of gel solute and nutrients.

The nutrient solution can also include plant growth hormones and other compounds serving to further increase the probability of germinant survival.

As used herein, a "nutrient liquid" is an aqueous solution of nutrients similar to the "MS liquid" formulation. A "nutrient agar" s similar to the "MS medium." Changes in types and amounts of certain ingredients can be made to meet the needs of specific types of plants without departing in any substantial manner from the purpose and utility of a nutrient liquid or nutrient medium.

Since nutrient media, nutrient liquids, and any nutrient-containing hydrated gel is a rich growth medium for microorganisms and fungi, and other possible plant pathogens, it is important that all such liquids, as well as other additives and the totipotent plant tissue itself, be sterile before use. Totipotent plant tissue is kept sterile by culturing under sterile conditions. Liquids can be autoclaved or microfiltered.

Hydrated Gel Containing an Oxygen Carrier

Totipotent plant tissue of different species of plants requires different amounts of oxygen to undergo germination. A hydrated gel in a manufactured seed according to the present invention can comprise an oxygen-carrier compound that can provide the hydrated gel with a concentration of oxygen that is higher than the concentration of oxygen, at standard temperature and pressure, that would otherwise be absorbed by the hydrated gel from the atmosphere. Such a gel comprising an oxygen-carrier is termed herein an "oxygen-carrying" gel.

The hydrated gel used in a manufactured seed according to the present invention can also have the capacity to acquire, particularly at time of sowing, a concentration of molecular oxygen therein that is higher than the concentration of molecular oxygen at standard temperature and pressure that would otherwise be present in the hydrated gel as a result only of absorption of molecular oxygen from the atmosphere.

Providing a hydrated gel with oxygen can be achieved by any of several representative methods, as disclosed extensively in, for example, U.S. Pat. Nos. 5,236,469, and 5,427,493, both incorporated herein by reference.

The minimum oxygen concentration required for germination of a manufactured seed is preferably at least adequate to support sufficient growth of the radicle (structure that eventually becomes the plant root) to effect germination of the radicle. Generally, if the oxygen concentration is high enough for germination of the radicle, it is also high enough to support germination of the shoot. The minimum concentration of oxygen seems to depend in part on the particular plant species represented by the totipotent plant tissue and on the particular configuration of the manufactured seed. The minimum oxygen concentration can be determined for a particular species and type of totipotent plant tissue, and for a particular embodiment of manufactured seed according to the present invention, by performing a simple germination experiment involving a series of otherwise identical manufactured seeds each of which having a stepwise different oxygen concentration from all other manufactured seeds in the series.

Candidate oxygen carriers can be selected from the group consisting of perfluorocarbons (PFCs) and silicone oils. Representative perfluorocarbons include perfluorocycloalkanes, perfluoro(alkylcycloalkanes), perfluoro(alkylsaturated heterocyclics), and perfluoro(tert-amines). These types of compounds are capable of absorbing large amounts of oxygen, and are also inert and substantially non-phytotoxic. Use of these compounds in hydrated gels is disclosed extensively in U.S. Pat. Nos. 5,236,469, and 5,427,593, cited above and incorporated herein by reference.

PFCs and silicone oils, if used, are preferably in the form of a stabilized emulsion in the hydrated gel. The emulsion is preferably stabilized by adding a substantially non-phytotoxic surfactant. Representative surfactants include methyl oxirane polymers, egg albumin, and other substantially non-phytotoxic surfactants such as those for food or ingestible pharmaceutical use.

The concentration of perfluorocarbon (or silicone oil) can depend on the oxygen requirements of the plant tissue in the manufactured seed, the oxygen-carrying capability of the perfluorocarbon (or silicone oil) being used, the type of hydrated gel, or the size of the microdroplets comprising the emulsion. Generally, if used, the concentration of the perfluorocarbon in the hydrated gel is about 15% w/v or less and the concentration of silicone oil in the hydrated gel is about 30% w/v or less.

The concentration of surfactant is dependent upon the surfactant being used and the size of the microdroplets comprising the emulsion. As the diameter of the droplets in a unit volume of perfluorocarbon emulsion is decreased, the surface area of the disperse phase is increased, and correspondingly more surfactant is required to suitably stabilize the emulsion. Generally, the concentration of surfactant is about 10% w/v or less.

Manufactured Seed Coat

The manufactured seed can include a manufactured seed coat that, like a natural seed coat, protects the totipotent plant tissue and other internal structures of the manufactured seed from mechanical damage, desiccation, from attack by microbes, fungi, insects, nematodes, birds, and other pathogens, herbivores, and pests, among other functions.

The manufactured seed coat can be fabricated from a variety of materials including, but not limited to, cellulosic materials, glass, plastic, moldable plastic, cured polymeric resins, paraffin, waxes, varnishes, and combinations thereof such as a wax-impregnated paper. The materials from which the seed coat is made are substantially non-toxic and preferably provide a degree of rigidity. It is preferable that the seed coat be biodegradable, although it is also preferable that the seed coat remain intact until after emergence of the germinating totipotent plant tissue. It is also preferable that, until after emergence, the seed coat be resistant to penetration by microbial or other plant pathogens.

Preferably, the seed coat has a portion possessing sufficient strength to prevent penetration by the germinating totipotent plant tissue (e.g., the radicle) and is preferably impermeable to gases, water, and soil microbes. Such a seed coat also preferably has a portion that can be penetrated by the germinating totipotent plant tissue, particularly the radicle. Preferably, the penetrable portion is an opening or orifice defined by the seed coat. Alternatively, the penetrable section is a region of the seed coat that is thin or weakened relative to other regions of the seed coat. In such manufactured seeds, it is preferable that the radicle of the totipotent plant tissue be oriented toward the opening or orifice so as to facilitate protrusive growth of the primary root of the germinating totipotent plant tissue from the manufactured seed. An end seal is preferably disposed across the opening. The end seal is penetrable or capable of being dislodged by the germinating totipotent plant tissue (particularly the radicle), yet provides sufficient physical restraint to retain the plant tissue within the protective seed coat during handling of the manufactured seed. The end seal is preferably a gas-permeable, water-impermeable membrane such as pre-stretched Parafilm® (American National Can, Greenwich, Conn.). Alternative materials include, but are not limited to, wax-impregnated cellulosic tissue and any of various thin polymeric films, e.g., Cellulon™.

If the seed coat configuration includes an opening with an end seal, an antibiotic can be placed under the end seal to prevent invasion by a bacterial or fungal pathogen or other pest. If the antibiotic is a beneficial microorganism, the microorganism can "inoculate" the primary root as it penetrates the end seal during germination.

If the seed coat lacks an opening or weakened or thin section, the seed coat must not prevent the totipotent plant tissue germinating from within from growing out of the manufactured seed without fatal or debilitating injury to the tissue. To this end, polymeric materials having a high dry strength and low wet strength can be used. The seed coat can also be so constructed that it breaks apart easily upon application of an outwardly protrusive force from inside the manufactured seed but is relatively resistant to compressive forces applied to the outside of the seed coat, e.g., a self-breaking capsule (see, e.g., Masuda and Sakamoto, JP 59102308, published 1993; Redenbaugh, Introduction, In: Redenbaugh (ed.), Synseeds: Application of Synthetic Seeds to Crop Improvement, Chapter 1, CRC Press, Boca Raton, Fla., 1993). However, such an embodiment is less preferred, since, when the seed coat breaks, the totipotent plant tissue can readily desiccate and is exposed to attack by pathogens, pests, and herbivores.

The seed coat can have two or more layers, each having the same or a different composition. For example, the innermost layer can comprise a relatively compliant and water-impermeable cellulosic material and the outer layer can comprise a polymeric material having a high dry strength and a low wet strength. Alternatively, the inner layer can comprise a rigid shape such as an open-ended cylinder, where at least a portion of the open end(s) is covered with an outerlayer material having a high dry strength and a low wet strength.

Further alternatively, the seed coat can comprise a relatively compliant cellulosic or analogous material, shaped to at least partially conform to the shape of the mass of hydrated gel to be disposed therein, and having at least one tapered end. The tapered end terminates with an orifice which is preferably covered with an end seal, as described above.

Additives such as plant nutrients, antibiotics, and plant-growth regulators can be added to the manufactured seed coat, for example, by incorporation into the material forming one or more of the layers of the seed coat or by coating or otherwise treating the layer(s) with the additive by conventional means.

Although it is preferred that a manufactured seed according to the present invention have a hydrated gel disposed within the manufactured seed coat, the gel can be absent. If the gel is absent, it is preferred that the manufactured seed coat be selected to prevent mechanical damage to the totipotent plant tissue, e.g., be rigid and physically support the plant tissue. If the gel is absent, it is also preferred that the manufactured seed coat prevent desiccation and penetration by pathogens and pests while allowing gas exchange, as is the case, for example, with a rigid seed coat having an opening covered by a gas-permeable, liquid-impermeable membrane such as Parafilm®.

Shoot Restraint

A manufactured seed according to the present invention preferably is configured so as to prevent entrapment of the shoot (and/or of structures situated at the rear of the shoot) within the manufactured seed, particularly in the artificial gametophyte. Such entrapment can prevent the growing plant from emerging from the manufactured seed, thereby causing abnormal growth and even death of the germinating plant tissue. Hence, a manufactured-seed configuration allowing "natural" emergence of the germinating plant tissue similar to what occurs with a natural seed is most preferred.

Preferred restraints include, but are not limited to, any of various tube-like structures surrounding and contacting the totipotent plant tissue, particularly all or part of the shoot end. The restraint, in turn, is disposed within the manufactured seed, e.g., in a cavity formed in the hydrated gel. The restraint permits transfer of water, nutrients, and oxygen from the gel to the totipotent plant tissue and, to such end, is preferably porous. The shoot end of the totipotent plant tissue is oriented toward a closed end of the tube and the radicle is oriented toward an open end. As the shoot elongates during germination, it impinges upon the closed end of the tube, which prevents entrapment of the shoot and urges the radicle to emerge from the open end of the porous tube. Thus, the germinating totipotent plant tissue emerges from the manufactured seed in a manner similar to germination of a natural botanic seed.

Generally, appropriate shoot restraint can be achieved via a number of ways including, but not limited to, the following:

(1) Enclosing the totipotent plant tissue in a preformed cylinder that contacts, and preferably at least partially surrounds the plant tissue (particularly the shoot end). The cylinder is preferably encapsulated in a hydrated gel ("artificial gametophyte"). The preformed cylinder is preferably porous and can be fabricated from suitable materials such as, but not limited to, glassy, metal, elastomeric, ceramic, clay, plaster, cement, starchy, putty-like, synthetic polymeric, natural polymeric, and adhesive materials.

(2) Forming a cavity in a hydrated gel "capsule" and attaching a porous material to the walls of the cavity before inserting a unit of totipotent plant tissue into the cavity. Candidate porous materials include, but are not limited to, dialysis tubing, natural sausage casing material, paper, fabric, and collagen materials.

(3) Forming a first cavity in a hydrated gel "capsule", filling the cavity with a conformable porous substance, then either forming a smaller-diameter second cavity in the porous substance coaxial with the first cavity before inserting a unit of totipotent plant tissue into the second cavity, or inserting the plant tissue directly into the porous substance in the first cavity. Alternatively, at least the shoot end of the plant tissue is dipped in the conformable porous substance before the plant tissue is inserted in the first cavity. Representative conformable porous materials include, but are not limited to, plaster of paris, cement, natural and synthetic polymers, tree resins, porous waxes, agar or alginate at a higher concentration than used for the gel capsule, and clays.

(4) "Hardening" the hydrated gel itself, such as before or after forming a cavity therein, then inserting a unit of totipotent plant tissue into the cavity. As used herein, "hardening" refers generally to making the gel comprising the artificial gametophyte stiffer or more rigid. Hardening can be effected by increasing the concentration of the gel solute used to make the hydrated gel, performing a "surface drying" of the hydrated gel, or by adding a particulate material to the gel. Candidate particulate materials include, but are not limited to, sand, plaster of paris, pulp fibers, cement, and polymeric substances.

(5) Inserting a sheet or piece of porous material between the plant tissue and the hydrated gel as the plant tissue is inserted into the gel. Candidate porous materials include, but are not limited to, paper, polymer-soaked paper, fabric, and polymer sheets.

(6) Forming a cavity in the hydrated gel, then applying a conformable porous coating on the walls of the cavity. Candidate coating materials include, but are not limited to, dry powdery materials such as plaster of paris or cement that, when wetted by liquid from the gel, form a porous barrier. Alternatively, a web-forming material can be applied to the walls of the cavity, such as gelatin powder, sponge material, natural webbing, and foams.

(7) Forming a gel capsule ("artificial gametophyte") using a sufficiently concentrated gel solution to prevent a unit of totipotent plant tissue germinating therein from growing into and becoming entrapped in the gel.

Antibiotics, Plant Growth Regulators

A manufactured seed according to the present invention can also comprise one or more well known antibiotics. The term "antibiotic" is intended to broadly encompass agents known in the art that kill, prevent or inhibit the growth of, or repel pathogens, pests, and herbivores that are detrimental to the growth and development of the totipotent plant tissue including, but not limited to, bacteria, yeast, fungi, nematodes, insects, rodents, and birds. The antibiotic can be either a chemical compound or a beneficial organism that is effective in inhibiting the colonization of pathogens or that produces antibiotics. For example, a beneficial microbe (e.g., Mycostop™, Kemira Agro Oy, Helsinki, Finland) can be placed near the site of emergence (e.g., an opening in the seed coat) of the primary root from the manufactured seed to colonize the root and preventing the root from becoming an area of entry for microbial pathogens in the soil. Microbes can also be added to enhance nutrient availability (e.g., nitrogen fixing bacteria or mycorrhizae) or otherwise to benefit the unit of totipotent plant tissue or the germinant developing therefrom. Antibiotics used in the practice of the present invention are compatible with growth and development of the totipotent plant tissue.

For example, a number of antibiotic compounds have been tested and found to be effective for use with totipotent plant tissue of Douglas fir as additives to the hydrated gel. These include (together with recommended dosages) the antimicrobial compounds benzylpenicillin (100 mg/L), vancomycin (100 mg/L), ticarcillin (100 mg/L), cefamandole (10 mg/L), gentamicin (10 mg/L), and rifampicin (15 mg/L); the antifungal compounds miconazole (1 mg/L), amphotericin (2.5 mg/L); and "combination" antibiotic/antimycotic agents such as "A 7292" (Sigma Chemical Co., St. Louis, Mo., containing 10 mg/ml streptomycin, 6.06 mg/ml penicillin, and 25 µg/ml amphotericin B). Other dosages of these compounds and other antibiotics known in the art, particularly those employed for treating botanic seeds, can be employed as well, whether alone or in combination.

An antibiotic can be present in any part of the manufactured seed. For example, the antibiotic can be added directly to the synthetic gametophyte (hydrated gel) or be incorporated into or used to coat one or more layers of the seed coat. If the antibiotic is toxic to the totipotent plant tissue at high concentrations, the antibiotic can be restricted to the seed coat alone (or an outermost layer of a multi-layer seed coat), for example.

Various plant-growth regulators, alone or in combination can also be added to the artificial gametophyte or one or more seed coats of the manufactured seed. Representative plant-growth regulators include auxins, cytokinins, gibberellins (e.g., $GA_3$, $GA_{4n}$, etc.), or other plant-growth regulators known in the art. It is preferred that such plant-growth regulators be present in the artificial gametophyte.

Long-Term Storage of Manufactured Seeds

The components of manufactured seed, particularly the totipotent plant tissue but also the artificial gametophyte, can germinate or decompose, respectively, if stored for extended periods under ambient conditions. However, depending on the composition of the various components of the manufactured seeds, manufactured seed can be prepared for long-term storage, e.g., (1) by storing the manufactured seed (or at least the totipotent plant tissue) in an environment containing a respiration-limiting gas and/or reduced oxygen concentration, preferably at reduced temperatures; or, alternatively, (2) by freezing and/or dehydration of the assembled seed or one or more of the components of the seed before assembly. These storage methods can be combined with each other and with other methods known in the art for preventing the germination of totipotent plant tissue while maintaining its viability, until time for sowing.

Storage after treatment with a respiration-limiting gas. A manufactured seed according to the present invention can be stored for extended periods of time in the presence of levels of a respiration-limiting gas sufficient to substantially reduce the respiration of the plant tissue and thus preventing germination, while maintaining viability of the plant tissue. The respiration-limiting gas is of a type and at a concentration effective to limit the respiration of the totipotent plant tissue, preferably effecting a substantial reduction in respiration of the tissue, and thereby prevent germination of the plant tissue until a desired time.

A "substantial" reduction in respiration is a reduction of at least approximately 10%, preferably at least approximately 25%, and more preferably at least 75% or more, relative to a control. Respiration rates can be measured by any of various methods known in the art, and can be indirectly determined by observing whether germination of the totipotent plant tissue has commenced after a given time in storage.

Any of a variety of well known respiration-limiting gases or mixtures thereof can be employed according to the present invention, e.g., nitrogen, carbon dioxide, or biologically inert gases (e.g., noble gases). The percentage of molecular oxygen in the respiration-limiting gas is preferably less than about 10% and more preferably less than about 5%. The respiration-limiting gas can limit respiration by a number of mechanisms, for example, by (1) reducing the relative concentration of molecular oxygen present in the gas environment of the totipotent plant tissue, e.g., by displacing molecular oxygen; or (2) by reversibly inhibiting the biochemical processes involved in respiration, e.g., by binding to oxygen-binding sites in cellular enzymes.

In order to prepare manufactured seed for storage, manufactured seed can be sparged with the respiration-limiting gas for a time sufficient to allow the concentration of the gas inside the seed to reach a respiration-limiting level. Sparging can be performed during manufacture of the manufactured seed, e.g., prior to or after insertion of the totipotent plant tissue. The respiration-limiting gas is can be introduced at atmospheric pressure or at a pressure greater than atmospheric pressure. The manufactured seed can optionally be placed under subatmospheric pressure (i.e., a partial vacuum) prior to introduction of the respiration-limiting gas under conditions suitable to maintaining viability of the plant tissue. The manufactured seed are preferably stored at atmospheric pressure. (Less preferably, the manufactured seed can be stored under subatmospheric pressure, with or without the presence of the respiration-limiting gas, with levels of molecular oxygen sufficient to maintain viability of the plant tissue but low enough to prevent germination.)

After sparging with a respiration-limiting gas, the manufactured seed are then preferably stored in a substantially gas-tight environment (e.g., a substantially sealed container) containing the same or a different respirating-limiting gas. Preferably, the seed are stored at a reduced temperature but above the freezing point of the plant tissue in order to improve the keeping quality of the seed, i.e., at less than about 20° C., preferably less than about 10° C., more preferably less than about 5° C., most preferably at about 0° C.

As described above, a manufactured seed according to the present invention preferably comprises a protective manufactured seed coat, which can be gas-impermeable, and which can define an opening over which is disposed an end seal. Such a seed coat can be conveniently sparged with a respiration-limiting gas after assembly of the manufactured seed, if the end seal is gas-permeable. Alternatively, the end seal can be disposed across the opening after sparging.

It is preferable that, when the period of seed storage is over, the respiration-limiting gas be vented from the container in which the seed is stored. Venting can be performed by purging the container with air or pure oxygen until the concentration of the respiration-limiting gas in the synthetic gametophyte has fallen, and the concentration of oxygen has increased, to levels conducive to germination. If the manufactured seed contains a synthetic gametophyte comprising an oxygen-carrying compound, e.g., a perfluorocarbon or silicone oil, the time for gas equilibration could be longer than for a synthetic gametophyte lacking such a compound. Perfluorocarbons, for example, have a higher solubility for most gases than does water, and thus are compatible with the use of rate-limiting gases.

Storage after dehydration and/or freezing. The term "dehydration" as employed herein refers to the process by which the water content of at least one component of a manufactured seed is reduced, preferably by 50% or more by weight. Totipotent plant tissue is preferably dehydrated to less than about 10% water content by weight.

The term "freezing" as employed herein refers to the process by which the temperature of at least one component of a manufactured seed is reduced to below the temperature at which the totipotent plant tissue component of the seed, if untreated, would normally freeze.

Totipotent plant tissue can be separately stored after freezing or dehydration or both and the manufactured seed assembled shortly before use. It is preferable that the totipotent plant tissue be frozen or dehydrated together with a shoot restraint, if such a shoot restraint is to be present in the manufactured seed.

The synthetic gametophyte and other components of the seed can also be frozen, dehydrated, or both, either before or after assembly of the manufactured seed. For example, the synthetic gametophyte can be frozen within a manufactured seed coat or frozen separately as a plug to be subsequently inserted in the seed coat. If the manufactured seed comprises a synthetic gametophyte in the form of a hydrated gel, particularly a hydrated gel containing an emulsion (e.g., an emulsion of a perfluorocarbon or silicone oil oxygen carrier), it is preferable to freeze at least the gametophyte portion of the manufactured seed rather than dehydrate it for long-term storage. Some hydrated gels can be difficult to completely rehydrate. Moreover, if the hydrated gel comprises an emulsion (e.g., a synthetic gametophyte containing an emulsified perfluorocarbon or silicone oil as an oxygen carrier), the emulsified material can coalesce upon dehydration in the absence of the stabilizing gel.

It is preferable to incorporate a nutrient source in the synthetic gametophyte, in order to ensure that the totipotent plant tissue has a ready nutrient supply upon germination. In such manufactured seeds, it is preferable that the seed include a manufactured seed coat or other means to prevent the loss of nutrients and prevent entry of microbes prior emergence of the germinant from the manufactured seed.

A manufactured seed that has been dehydrated (or dehydrated and frozen) for long-term storage can be imbibed in a biologically compatible aqueous solution such as water before sowing.

If the manufactured seed is to be stored by freezing, it is preferred that the totipotent plant tissue (preferably together with the shoot restraint) be separately frozen, then inserted into the frozen hydrated gel before long-term storage. It is preferable that the totipotent plant tissue be dehydrated before freezing to reduce damage to plant tissues as a result of ice crystal formation caused by freeze-thaw cycles during storage. Alternatively, the totipotent plant tissue can be treated before freezing with a cryoprotectant, i.e., a substance that prevents the formation of tissue-damaging ice crystals and is compatible with the growth and normal development of the totipotent plant tissue. Appropriate cryoprotectants include, but are not limited to, the following, alone or in combination: thermal hysteresis proteins (see U.S. Pat. No. 5,358,931, incorporated herein by reference), polyhydric alcohols (e.g., glycerol, ethylene glycol, propanediol, butanediol, butanetriol); dimethyl sulfoxide; polyvinylpyrrolidone; glucose; sucrose; and carboxymethyl cellulose. Suitable concentrations of such substances can vary widely, depending on, inter alia, the plant species, concentrations of other components present, the cooling rate, and the lowest temperature reached, but are preferably from about 5% to about 35% by weight. The cryoprotective substance (e.g., in aqueous solution) is placed in contact with the totipotent plant tissue, preferably by immersing the totipotent plant tissue in the substance, preferably throughout the time the totipotent plant tissue is exposed to temperatures below the normal freezing point of the tissue. Alternately, the totipotent plant tissue can be produced from a plant that has been genetically engineered to express a cloned thermal hysteresis protein by conventional methods.

A preferred method of preparing a manufactured seed for long-term storage comprises the following steps:

(1) Prepare a manufactured seed coat and partially fill the seed coat with a synthetic gametophyte, thereby producing a manufactured seed "capsule" (lacking a unit of totipotent plant tissue).

(2) Freeze the capsule, preferably to below about −3° C., more preferably to below about −10° C., by conventional freezing methods, e.g., using dry ice, liquid nitrogen, or an on-line freezer.

(3) Place a unit of totipotent plant tissue in a shoot constraint.

(4) Dehydrate the totipotent plant tissue and shoot restraint, preferably to a water content of less than about 10% or less. Conventional drying methods can be employed, e.g., use of a chemical desiccant such as $Ca(NO_3)_2$ to create a drying environment in which the totipotent plant tissue is kept until dry.

(5) Freeze the dehydrated totipotent plant tissue, preferably to below about −3° C., more preferably to below about −10° C. Conventional freezing methods can be used, preferably quick-freezing methods, e.g., using dry ice, liquid nitrogen, or an on-line freezer.

(6) Finish assembly of the manufactured seed at a temperature sufficiently low to avoid rehydration of the totipotent plant tissue, preferably below about −3° C., more preferably below about −10° C.

(7) Store the assembled seed at a temperature at or below the normal freezing temperature of the plant tissue, preferably 0° F. or colder.

By "normal freezing temperature" is meant the temperature at which ice crystals would normally form in the plant tissue, assuming the plant tissue is not dehydrated and the plant tissue has not been treated with a cryoprotectant, as discussed above.

Upon thawing, e.g., by exposure to room temperature, the water in the frozen synthetic gametophyte permeates the totipotent plant tissue and initiates the preliminary biochemical processes of germination. The seed are then sown.

Desiccation and freezing of the manufactured seed parallels the process by which a botanic seed is formed and survives cold winter temperatures. In a preferred method of long-term storage of the manufactured seed of the present invention, the totipotent plant tissue alone is desiccated, as in true seed. Desiccation of totipotent plant tissue alone is a common practice in embryogenesis protocols and can be performed without loss of viability, as described, for example, in U.S. Pat. No. 5,284,765. The gametophyte, while not desiccated, is prevented in its frozen state from supplying the totipotent plant tissue with nutrients or water required for germination, as is the case with a true gametophyte, which cannot hydrate the totipotent plant tissue due to its dryness.

Structural Embodiments of Manufactured Seeds

Various possible embodiments of manufactured seeds within the scope of the present invention are disclosed in U.S. Pat. No. 5,236,469, incorporated herein by reference.

Embodiments of FIGS. 1–3. After preparing the gel liquid, preparing units of cured hydrated gel for use in making manufactured seeds can be done in a number of ways. Fluid transfer between the totipotent plant tissue and the hydrated gel can be accomplished, e.g., by direct contact or via an intervening water-permeable "bridge" such as filter paper. In general, the totipotent plant tissue can rest on a surface of a unit of hydrated gel, rest in a preformed hole or cavity in a block of hydrated gel, or be entirely encapsulated in the hydrated gel. In the first two embodiments, the gel is cured preformed into a preferred shape, or can be formed as a larger cured mass and cut to size before inserting the totipotent plant tissue. In the case of totally encapsulating a unit of totipotent plant tissue in the hydrated gel, the totipotent plant tissue can be inserted in a unit of gel having the desired volume before the gel is completely cured.

FIG. 1A is a cross-sectional view of one embodiment of a manufactured seed 10 made by totally encapsulating a unit of totipotent plant tissue 12 in a hydrated gel capsule 14.

Figure 1B:
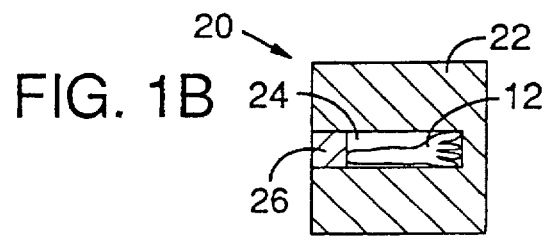
FIG. 1B is a cross-sectional view of an alternative embodiment of the manufactured seed shown in FIG. 1A.

FIG. 1B is a cross-sectional view of another embodiment of a manufactured seed 20 wherein a large portion 22 of the unit of hydrated gel is preformed. In FIG. 1B, the large portion 22 is shown in the shape of a cube, although other shapes will also suffice, such as spherical or ovoid. The larger portion 22 has a bore 24, which can also be preformed or cut after forming, into which the totipotent plant tissue 12 is inserted. If desired, the bore 24 can be sealed with a plug 26 after inserting the totipotent plant tissue 12. The plug 26 can be made of an additional piece of cured hydrated gel or other suitable material such as paraffin or similar material.

Figure 1C:
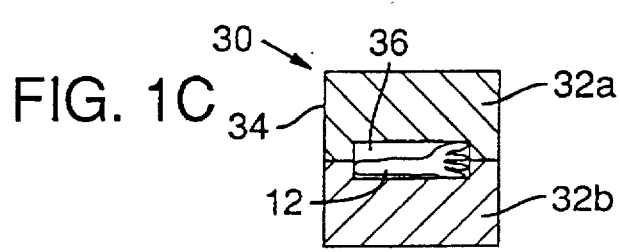
FIG. 1C is a cross-sectional view of another alternative embodiment of the manufactured seed shown in FIG. 1A.

As can be seen in FIG. 1C, the manufactured seed 30 can be made by preforming two opposing capsule halves 32a, 32b which, when pressed together to form a complete "capsule" 34, define a cavity 36 for receiving the totipotent plant tissue 12.

Figure 2A:
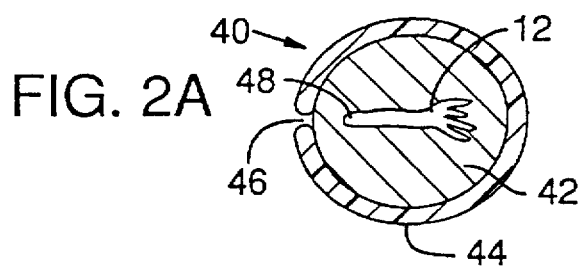
FIG. 2A is a cross-sectional view of a manufactured seed similar to that shown in FIG. 1A but also including a manufactured seed coat.

FIG. 2A shows a cross-sectional view of a manufactured seed 40 comprising totipotent plant tissue 12, a "capsule" 42 comprised of a hydrated gel in surrounding relationship to the totipotent plant tissue 12, and a manufactured seed coat 44 in surrounding relationship to the gel capsule 42. The seed coat 44 preferably also has an opening 46 toward which the radicle 48 of the totipotent plant tissue 12 is oriented so as to facilitate protrusive growth of the radicle 48 from the manufactured seed 40 during germination and prevent entrapment of the radicle inside the manufactured seed 40.

Figure 2B:
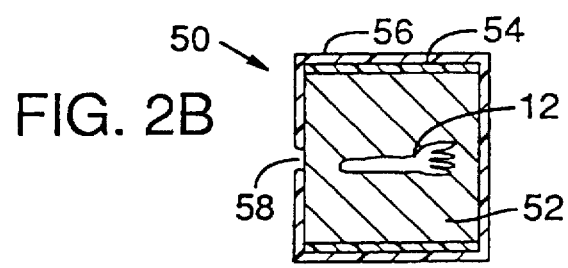
FIG. 2B is a cross-sectional view of an alternative embodiment of the manufactured seed shown in FIG. 2A.

FIG. 2B shows a cross-sectional view of a manufactured seed 50 comprising totipotent plant tissue 12 and a "capsule" 52 comprised of a hydrated gel in surrounding relationship to the totipotent plant tissue 12, where the capsule 52 is cast in a seed coat comprising an inner shell 54, to create a particular shape, such as a cylinder, and an outer layer 56 that is similar to the manufactured seed coat 44 of FIG. 2A. The inner shell 54 can be cut, for example, from a plastic or cellulosic drinking straw or analogous material such as glass tubing. Then, the capsule-containing inner shell 54 is coated or otherwise layered with the outer layer 56. Again, it is preferable that the seed coat include an opening 58 to ease protrusion of the germinating radicle. It is also preferable that the outer layer 56 have a low wet strength and a high dry strength.

Figure 2C:
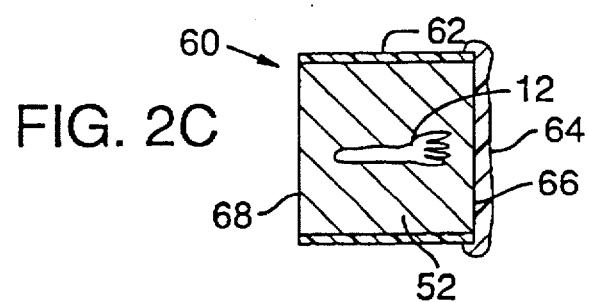
FIG. 2C is a cross-sectional view of another alternative embodiment of the manufactured seed shown in FIG. 2A.

Another gel "capsule" surrounding a unit of totipotent plant tissue and having a manufactured seed coat is illustrated in FIG. 2C, which shows a cross-sectional view of a manufactured seed 60. As in FIG. 2B, the FIG. 2C embodiment comprises totipotent plant tissue 12, a capsule 52 comprised of a hydrated gel in surrounding relationship to the totipotent plant tissue 12, and a seed coat comprising a rigid cylindrical shell 62 similar to the inner shell 54 of FIG. 2B. In addition, a cap 64 of paraffin or other polymeric material is applied to at least the first end 66 to afford protection against desiccation and physical trauma as well as to properly restrain the shoot end of the plant tissue to facilitate normal germination. A second cap (not shown) similar to the first cap 64 can also be applied to the second end 68 for additional protection. If the seed coat 62 is made from a water-impermeable substance, it is preferable that the cap 64, especially if applied to both ends 66, 68, be made from a water-permeable substance to ensure adequate water penetration to the totipotent plant tissue 12 to support germination.

FIGS. 3A–3C show cross-sectional views of three further embodiments having a substantially bullet shape. FIG. 3A shows schematically a manufactured seed 70 comprising a block 71 of hydrated gel. The gel block 71 defines a shelf 72 on which is placed a unit of totipotent plant tissue 12 having a radicle 48 oriented toward the tapered first end 73 of the seed 70. In addition, the seed 70 is shown having an optional separate nutrient unit 74 in contact with the gel block 71 and containing plant nutrients. The nutrient unit 74 can have any of a number of possible forms, including a hydrated gel containing dissolved nutrients, a mass of microencapsulated nutrients, a mass of slowly-soluble nutrient compounds, and other possible embodiments. Alternatively (not shown), the gel block 71 could occupy a larger space in the seed 70 and also include nutrients dispersed throughout the gel block 71, thereby obviating the need for a separate nutrient unit 74.

FIG. 3A also shows an manufactured seed coat 75 in surrounding relationship to the block 71 and nutrient unit 74 as well as the totipotent plant tissue 12. To permit use of commonly available materials as the seed coat 75, such as tubular materials, the seed coat 75 preferably has a circular transverse cross-section, giving the outer shell 75 a cylindrical shape with a tapered first end 73 and a second end 76. The seed coat 75 can be constructed of, for example, a cellulosic tubular material similar to a paper drinking straw. Other materials such as plastic are also suitable. The tapered first end 73 can be formed via radial crimps 77 or other constriction method to reduce the diameter of the seed coat 75 at the tapered first end 73. The second end 76 can be similarly tapered (not shown) or it can be shaped as shown as a transverse circular flat contiguous with the seed coat 75. The tapered first end 73 preferably terminates with an orifice 78 toward which the radicle 48 is urged to grow by the tapered first end 73 during germination. If required, the orifice 78 can be occluded with a covering 79 comprised of a soft material such as paraffin or a material having a high dry strength and a low wet strength. Alternatively, the covering 79 can be comprised of a material that breaks apart easily upon application of a protrusive force from inside the capsule.

During sowing (not shown), the manufactured seed 70 can be deposited in soil or analogous plant-growing medium in any orientation. In the instance where the covering 79 has a low wet strength, subsequent irrigation would moisten and soften the covering 79 and allow the radicle 48 of the germinating totipotent plant tissue 12 to escape from the seed 70 into the soil.

FIGS. 3B and 3C schematically show alternative embodiments of the seed configuration shown in FIG. 3A. In FIG. 3B, totipotent plant tissue 12 is fully embedded in a block 81 comprising a hydrated gel. A separate nutrient-containing unit 84 is shown contacting the gel block 81. However, as in the FIG.-3A embodiment, the nutrients can be included in the gel block 81, which obviates the need for a separate nutrient unit 84. Surrounding the gel block 81 and the nutrient unit 84 is a seed coat 85 shaped similarly to the seed coat 75 of FIG. 3A. The radicle 48 of the totipotent plant tissue 12 points toward the tapered first end 83 of the seed coat 85. The tapered first end 83 terminates with an orifice 88 which is shown lacking the covering 79 of FIG. 3A to further illustrate possible embodiment variations. The FIG.-3B embodiment is preferred over the FIG.-3A embodiment because the totipotent plant tissue 48 is secured against losing contact with the gel block 81.

The FIG.-3C embodiment is similar to the FIG.-3B embodiment with respect to the bullet shape of the seed 90. The seed 90 comprises a nutrient unit 94, and a seed coat 95 having a tapered first end 93 which terminates with an orifice 98 and second end 96. A hydrated gel block 91 in which the totipotent plant tissue 12 is embedded is shown as an ovoid shape rather than the cylindrical shape of the gel block 81 in FIG. 3B. The FIG.-3C embodiment illustrates that the gel block 91 containing the totipotent plant tissue can be formed separately instead of being cast in the seed coat as suggested in FIG. 3B. The separate nutrient unit 94 can be eliminated by incorporating the nutrients into the gel comprising gel block 91.

In the interest of clarity, FIGS. 3A and 3B show the tapered first ends 73 and 83, respectively, located some distance away from the radicle 48. However, it is preferable, as shown in FIG. 3C, that the tapered first end 93 be located as close as possible to the radicle 48. This ensures that, during germination, the radicle 48 has only a minimal distance to elongate before being urged toward the orifice 98 by the tapered first end 93. Otherwise, geotropism of an elongating radicle could cause the radicle 48 to grow away from the tapered first end 93 and make it difficult for the tapered first end 93 to urge the radicle to grow toward the orifice 98.

FIG. 3D shows the exterior of an alternative embodiment 90a of the seed 90 of FIG. 3C, comprising a seed coat 95a, a tapered first end 93a, and a second end 96a corresponding to similar features shown in FIG. 3C. In FIG. 3D, the tapered first end 93a has a flat crimp 99 rather than the bullet-shaped configuration shown in FIG. 3C. As in FIG. 3C, the radicle of the totipotent plant tissue (not shown) inside the capsule 90a of FIG. 3D is oriented toward the tapered first end 93a, particularly toward an opening 98a left in the crimp 99.

Figure 4:
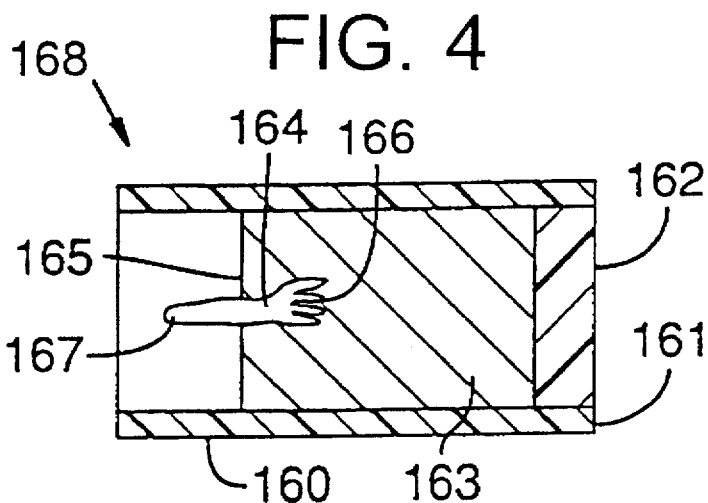
FIG. 4 is a cross-sectional view of a manufactured seed in which totipotent plant tissue is inserted into a block of hydrated gel, which is then surrounded by a rigid manufactured seed coat.
Figure 5:
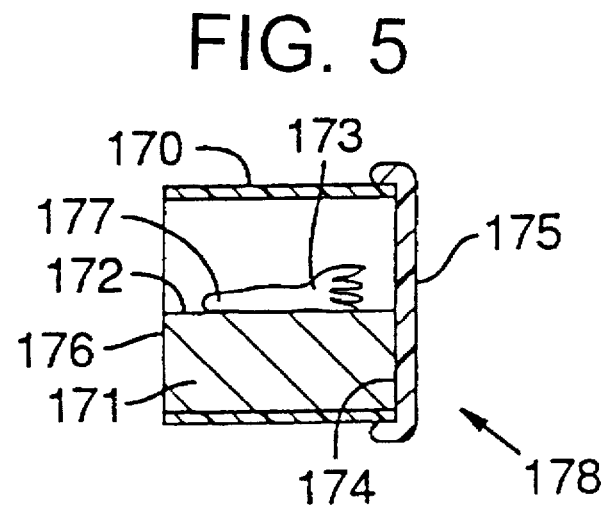
FIG. 5 is a cross-sectional view of a manufactured seed in which totipotent plant tissue is placed on the surface of a unit of hydrated gel, which is then surrounded by a rigid manufactured seed coat.
Figure 6:
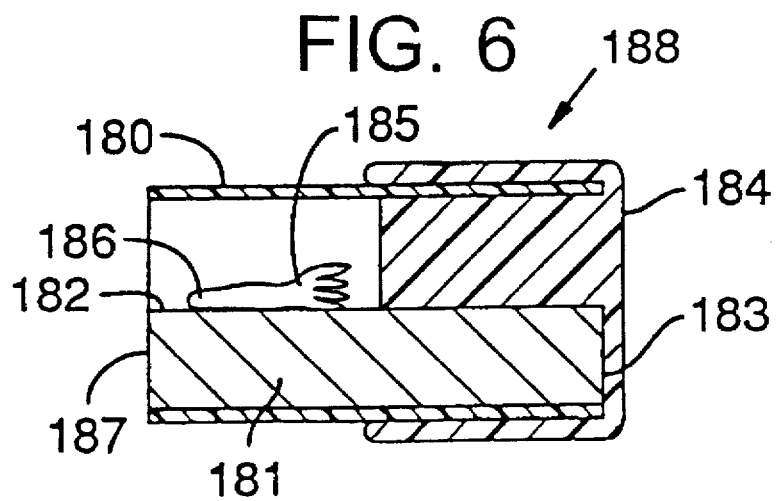
FIG. 6 is a cross-sectional view of an alternative embodiment of a manufactured seed in which totipotent plant tissue is placed on the surface of a unit of hydrated gel, which is then surrounded by a rigid manufactured seed coat.

Embodiments of FIGS. 4–6. FIGS. 4–6 show manufactured seed in each of which the totipotent plant tissue (e.g., conifer somatic) is individually inserted halfway into blocks of hydrated gel or individually placed on the surface of a unit of hydrated gel. Each unit of the gel is then surrounded by a seed coat comprising a rigid protective "shell" made of either thin transparent plastic or glass.

As shown in FIG. 4, the seed coats 160 comprising glass cylindrical shells were made each having a length of about 12 mm, an outside diameter about 7 mm, and an inside diameter about 5.6 mm. One end 161 of each seed coat was sealed with an elastomeric septum 162. After sterilization, the seed coats were oriented vertically open-end up and filled about two-thirds full with a hydrated gel 163. The totipotent plant tissue 164 was inserted halfway into the exposed gel surface 165 in each seed coat, shoot end 166 first, leaving the radicle 167 exposed to the atmosphere. The resulting seeds 168 were turned on their sides on a nutrient agar surface for incubation. In some embodiments, after inserting the totipotent plant tissue in the gel, the open ends of the seed coats were subsequently partially sealed from the atmosphere using a gas-permeable, water-impermeable membrane (e.g., pre-stretched Parafilm®). The film was applied to the open end in a manner that left a small hole through which the radicle could protrude during germination.

As shown in FIG. 5, rigid seed coats 170 were made by cutting a 4 mm diameter clear plastic drinking straw to 4 mm lengths. After sterilization, each seed coat 170 was oriented horizontally and filled about half full with a hydrated gel 171, leaving a flat gel surface 172 inside each seed coat extending the length of the seed coat. A unit of totipotent plant tissue 173 was placed on the gel surface (or "shelf") inside each seed coat. One end 174 of each seed coat was sealed using paraffin 175; the other end 176 was left open to the atmosphere, where the radicle 177 of the totipotent plant tissue 173 therein pointed toward the open end 176. The resulting seeds 178 were placed on their sides on a nutrient agar surface for incubation. Again, the open end of the seed coat can be partially sealed using pre-stretched Parafilm®.

As shown in FIG. 6, rigid seed coats 180 were made by cutting a 4 mm diameter clear plastic drinking straw to 8 mm lengths. After sterilization, each seed coat 180 was oriented horizontally and filled about half full with a hydrated gel 181, leaving a flat gel surface 182 inside each seed coat extending the length of the seed coat. One end 183 of each seed coat was sealed by dipping to a depth of 4 mm in paraffin 184, thereby causing the paraffin 184 to occupy about half the air space inside the seed coat. A unit of totipotent plant tissue 185 was placed on the gel surface 182 (or "shelf") inside each seed coat, with the radicle 186 pointing toward the open end 187, which was left exposed to the atmosphere. The resulting seeds 188 were placed on their sides on a nutrient agar surface during germination. Again, the open capsule ends can be partially sealed using pre-stretched Parafilm®.

Figure 7:
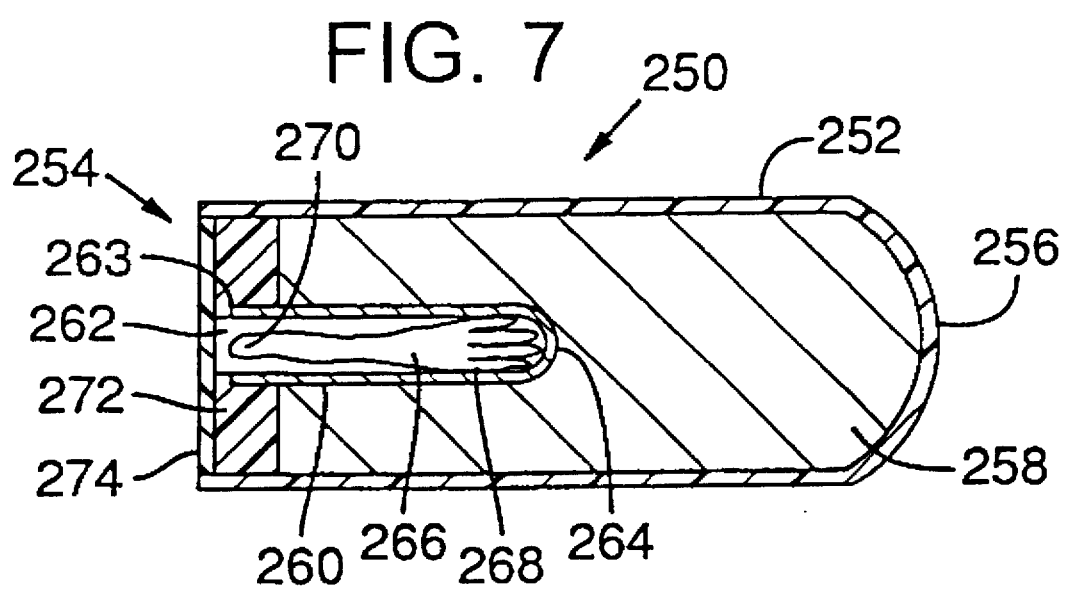
FIG. 7 is a sectional view of a preferred embodiment of a seed analog with provision for shoot restraint.

Embodiment of FIG. 7. A preferred embodiment of a manufactured seed offering shoot restraint according to the present invention is shown in FIG. 7, wherein a manufactured seed 250 comprises a seed coat 252 substantially surrounding a hydrated gel 258 that serves as an artificial gametophyte for the unit of totipotent plant tissue 266. The seed coat 252 provides physical protection for the interior of the manufactured seed 250 while allowing the germinant that develops from the plant tissue 266 to escape from the manufactured seed during germination.

The seed coat 252 has an open end 254 and a closed end 256. The seed coat 252 can be constructed, for example, of a thin plastic material or a cellulosic material such as a portion of a common paper soda straw about 6.5 mm in diameter and 10–20 mm long that has been made water resistant by such means as dipping in a suitable liquid hot wax such as melted paraffin. A seed coat 252 made of cellulose or other biodegradable material is preferred so that nursery beds will not be cluttered with spent seed coats from previous crops, although it is preferred that the seed coat remain intact at least until emergence of the primary root.

The closed end 256 can be created by the use of a suitable plug or barrier or preferably simply by crimping to form a somewhat dome-shaped or conical end. A seed coat 14 to 18 mm long length will hold about 0.8 ml of gel. A volume of gel from 0.5 to about 1.0 ml is usually very satisfactory.

The hydrated gel 258 can be any of the types of gels discussed hereinabove, optionally comprising nutrients and oxygen carriers. A preferred gel 258 is agar-based because agar will gel (i.e., "set" or "cure") spontaneously by lowering the temperature. The hydrated gel 258 should be somewhat firm to prevent seepage of liquid from the gel into the cavity 262 containing the plant tissue. Flooding of the cavity 262 can cause low percentage of normal germinants. An agar concentration of about 1.8 g/L has proved to be very satisfactory.

The size of the seed coat 252 can vary, depending upon the species of plant being propagated. The dimensions and gel capacities recited above are suitable for propagation of totipotent plant tissue of conifers and should not be considered limiting for this or other types of plants.

The plant tissue 266 is contained within an inner tube 260 to provide, at least in part, sufficient shoot restraint. The inner tube 260 has an open end 263 and a closed end 264. The plant tissue 266 is situated within the manufactured seed 250 so as to orient the shoot 268 toward the closed end 264 and the latent radicle 270 toward the open end 263.

The tube 260 can be made of various materials that are not phytotoxic and that permit adequate access of the totipotent plant tissue 266 to moisture, gases, and nutrients necessary for germination. Materials such as, but not limited to, filter paper, plaster of paris, ceramics, and reasonably rigid open-celled foams have all proved satisfactory. A tube made from filter paper or similar material can optionally contain small perforations. For somatic embryos of conifers, a tube length of 4 to 8 mm and an internal diameter of about 1.5 to 3 mm has proven very satisfactory.

The internal diameter of the tube 260 should be sufficient to allow a somewhat enlarged shoot portion 268 to be in intimate contact with the walls of the tube 260. The tube 260 allows access of nutrients, gases, and liquids necessary for germination to the plant tissue. As stated above, the hydrated gel 258 should be firm enough to prevent excess liquid from seeping from the gel 258 into the cavity 262 occupied by the plant tissue 266.

The seed coat 252 can be filled with the hydrated gel 258 by any of a number of means that will apparent to those of ordinary skill in the art. A preferred method, especially for automated processes, is by use of an automatic pipette or syringe pump. Each seed coat 252 is filled to within a few millimeters of the open end 254 and the gel 258 allowed to set by cooling (if, e.g., agar is used) or by ion exchange (if sodium alginate is used).

A coaxial internal cavity is formed in the hydrated gel 258 to accept the tube 260. The cavity can be molded in the gel as the gel cures or formed after the gel has cured. Forming the cavity after the gel cures can be performed in a number of ways. For example, a thin-walled cylindrical steel tube used as a punch has proved very suitable. The gel core left within the steel tube can be readily removed by application of vacuum. The cavity thus formed in the cured gel should have an internal diameter about equal to the outside diameter of the tube 260 so that intimate contact therebetween is maintained. The tube 260 can be inserted into the cavity by use of a mandrel.

After forming or inserting the tube 260 in the cavity, the plant tissue 266 can be inserted into the tube 260 shoot-end first.

A primary end seal 272 is preferably applied over the gel surface and around the protruding open end 263 of the tube 260 before insertion of the plant tissue in the gel. However, the primary end seal 272 should not cover the open end 263 of the tube 260. This result can be readily achieved by inserting an appropriate mandrel in the end of tube 260 while the primary end seal 272 is being formed.

Many materials are suitable for the primary end seal 272. Ordinary paraffin wax has proved very satisfactory. The primary end seal 272 is typically 2 to 4 mm thick but this is not in any way critical.

Preferably, a secondary end seal 274 is applied so as to cover the open end 263 of the primary end seal 272. The secondary end seal 274 is preferably very thin, most typically no more than about 1 mm thick. It can be made of the same material as the primary end seal 272. For example, one way to form the secondary end seal 274 is to heat the surface of the primary end seal 272 sufficiently to cause surface melting thereof and draw a small amount of the molten material to form a film across the open end 263. Preferably, the secondary end seal 274 is a gas-permeable, water-impermeable membrane such as pre-stretched Parafilm®, which can be sealed in place across the open end 263 by heat annealing or mechanical pressure.

As with the seed coat 252, an antibiotic can optionally be added to or inside the primary and secondary end seals.

The closed end 264 on the tube 260 has been found to be advantageous. The closed end 264 prevents the shoot end 268 growing inside the tube 260 from penetrating the tube and expanding into the gel 258. Expansion of the shoot end 268 into the gel 258 causes its entrapment in the gel in a manner preventing the growing plant from escaping from the manufactured seed. Such entrapment is believed to be a significant cause of germinant abnormalities. The growing shoot end is preferably only temporarily restrained within the tube 260. As it grows and elongates, the shoot end bears against the internal surfaces of the tube; this urges the shoot end out of the tube and, consequently, out of the hydrated gel. In this regard, the FIG. 7 embodiment effectively simulates a natural seed.

Figure 8:
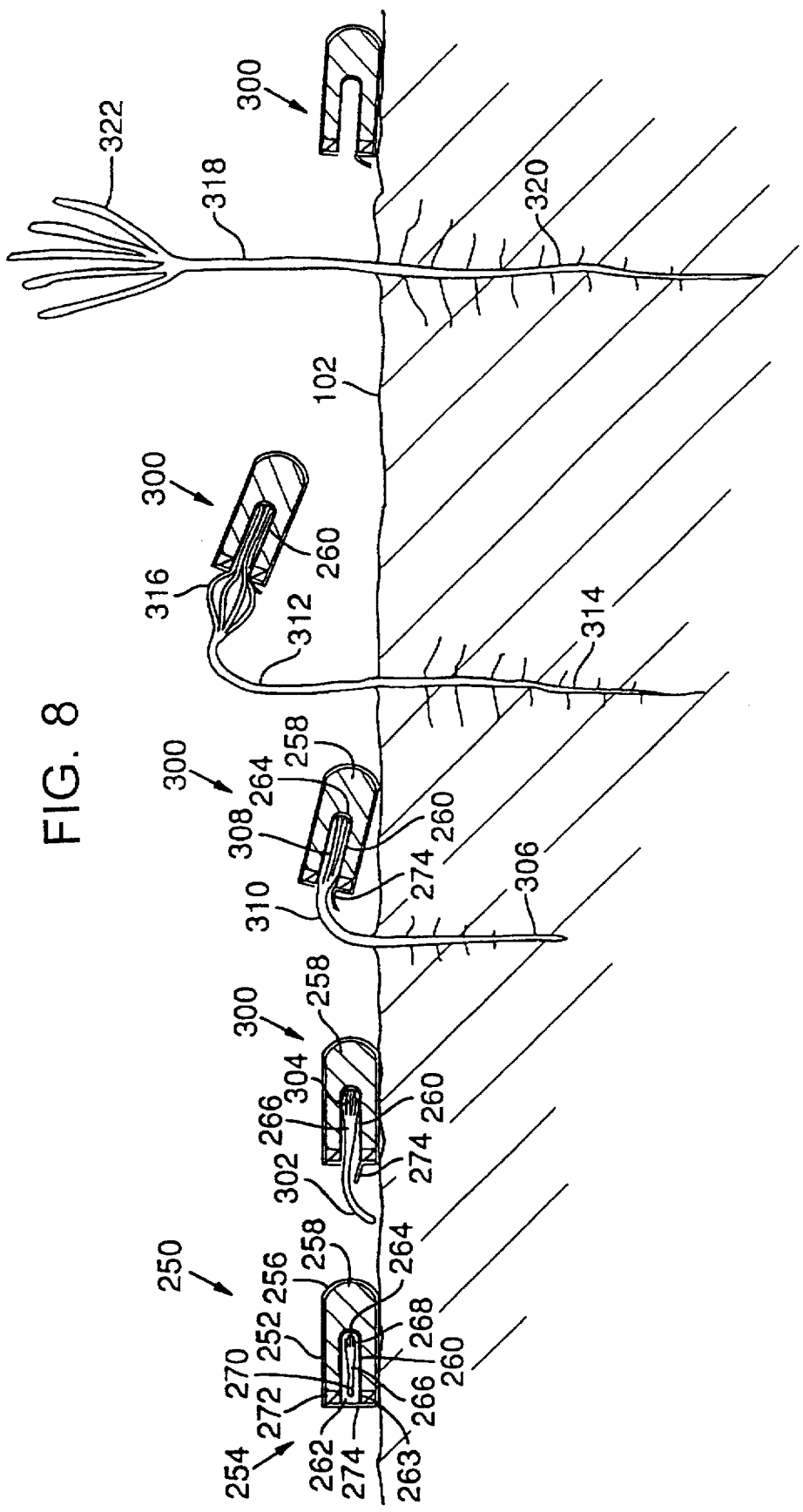
FIG. 8 is a stepwise sequential diagram illustrating germination of the FIG.-7 embodiment of a manufactured seed.

FIG. 8 shows a stepwise germination sequence of a gymnosperm embryo 266 from the embodiment of a manufactured seed 250 shown in FIG. 7. The first, or leftmost, image shows the manufactured seed 250 resting on the surface 102 of soil or analogous plant-growth medium. The manufactured seed 250 is shown, for simplicity, having been "sown" on the surface 102. However, it will be appreciated that the manufactured seed 250 can also be sown beneath the surface 102. In the leftmost image, reference designators are identical to those used in FIG. 7.

In the second image from the left, germination has begun and the growing radicle 302 has undergone sufficient growth to burst open the secondary end seal 274. Thus, the radicle 302 begins to grow outward and downward from the "capsule" 300 so as to eventually form a root anchoring the germinant in the soil. At the onset of germination, before the germinating embryo 266 bursts from the manufactured seed 250, nutrients (if any), oxygen and other gases, and water in the gel 258 ("artificial gametophyte") pass from the gel 258 to the embryo 266. Immediately after the growing radicle 302 has burst open the secondary end seal 274, atmospheric oxygen can enter the cavity 262 to provide oxygen to the embryo 266. It can also be seen in the second image that the cotyledons 304 have begun to enlarge and elongate, whereupon they bear against the inside walls of a restraint 260 to facilitate escape of the radicle 302 from the capsule 300.

In the middle image of FIG. 8, the radicle has further elongated and entered the soil to form a root 306. The cotyledons 308 have further elongated and are continuing to bear against the inside walls of the restraint 260, including the closed end 264 of the restraint, thereby further facilitating a "natural" germination. Nutrients (if any), water, oxygen, and other gases from the gel 258 continue to pass to the germinant 310. The restraint 260 prevents the cotyledons 308 growing within the restraint 260 from penetrating the restraint 260. Thus, the cotyledons 308 are prevented from becoming entrapped in the gel 258.

In the fourth image from the left in FIG. 8, the germinant 312 has further grown to have a longer root 314 and (although not always the case) lift the "capsule" 300 off the surface 102. The cotyledons assume a natural "bird cage" appearance as they further elongate out of the restraint 260.

Finally, in the rightmost image, the germinant 318 has become fully upright and has shed the "capsule" 300 in a manner analogous to the natural shedding of the remains of a botanic seed by a healthy germinant therefrom. The root 320 has continued to grow downward and the cotyledons 322 have spread apart. The germinant 318 has excellent prospects for developing into a healthy plant.

Further Definitions

The following terms as used herein are defined as follows:

"Somatic embryo" is a plant embryo that developed via the laboratory culturing of totipotent plant cells or by induced cleavage polyembryogeny.

"Zygotic embryo" is a plant embryo removed from a seed of the corresponding plant.

"Germinant" is a unit of totipotent plant tissue that has undergone sufficient growth and development to emerge from a seed coat, analogous to emergence from a natural botanic seed.

"Radicle end" is that part of a unit of totipotent plant tissue that develops into the primary root of plant.

"Shoot" or "shoot end" is that part of a unit of totipotent plant tissue that develops into the aerial portions of the plant and includes the cotyledon(s), epicotyl, and/or hypocotyl.

"Cotyledon" refers generally to the first, first pair, or first whorl (depending on the plant type) of leaf-like structures on a plant embryo that function primarily to make food compounds in the seed available to the developing totipotent plant tissue but in some cases act as food storage or photosynthetic structures.

"Hypocotyl" is that portion of a plant embryo or seedling located below the cotyledons but above the radicle.

"Epicotyl" is that portion of the plant developed after germination from the stem apex.

"Capsule" refers to a manufactured seed exclusive of the unit of totipotent plant tissue therein.

"Hypocotyl length" pertains to the length of the hypocotyl at the time the hypocotyl was measured.

"Hypocotyl germination" denotes the emergence of a shoot from the capsule, caused by elongation of the hypocotyl sufficiently to burst the capsule. This term does not take into consideration any length criteria or lack of hypocotyl malformations.

"Swollen hypocotyl" is an attribute of an abnormal germinant characterized by the hypocotyl or a portion thereof having a greater than normal diameter compared with hypocotyls on control bare "germinants" grown on the surface of a nutrient agar or similar nutrient medium.

"Twisted hypocotyl" is an attribute of an abnormal germinant characterized by the hypocotyl having grooves spiraling longitudinally up or down the length of the hypocotyl. This defect is usually found only in germinants exhibiting swollen hypocotyls.

"Swollen cotyledons" is an attribute of an abnormal germinant of a gymnosperm characterized by unusually large cotyledon(s) compared to cotyledons on control bare "germinants" grown on the surface of a nutrient agar or similar nutrient medium.

"Twisted cotyledon" is an attribute of an abnormal germinant of a gymnosperm characterized by the cotyledon(s) having a spiraled or twisted appearance.

"Radicle length" pertains to the length of the radicle at the time the radicle is measured.

"Radicle germination" denotes the emergence or protrusive growth of the primary root from the capsule, caused by elongation of the radicle sufficient to burst the capsule. This term does not take into consideration any length criteria.

"Growth through seed coat" occurs when a unit of totipotent plant tissue inside the manufactured seed coat undergoes elongation both of the radicle and the hypocotyl and bursts the seed coat at both ends. This is usually evidenced by the seed coat remaining for a period of time as a captive body around the hypocotyl.

"Normalcy" denotes the presence of all parts (radicle, hypocotyl, cotyledon(s), epicotyl) of a germinant at time of evaluation. In the case of gymnosperms, a normal radicle has length greater than 3 mm and no visibly discernable malformations compared to the appearance of control bare "germinants" grown on the surface of nutrient agar or similar nutrient medium.

EXAMPLE

The following example is based on the manufactured seed design comprising a unit of totipotent plant tissue, seed coat, restraint, and hydrated gel as shown in FIG. 7. The manufactured seeds can be exposed to a respiration-limiting gas mixture having a reduced level of oxygen and an increased level of nitrogen (relative to atmospheric) for a time sufficient to equilibrate the concentration of oxygen and nitrogen in the gel with that in the gas mixture.

Manufactured seed (lacking totipotent plant tissue) can be tested by equilibrating the capsule with any of various test gas mixtures in the same fashion. The totipotent plant tissue is then inserted into the capsule just before sowing. In this case, the totipotent plant tissue is either (1) desiccated and stored separately in the respiration-limiting gas mixture or (2) fresh.

After infusing the manufactured seed with the respiration-limiting gas mixture, the seed are sealed in an airtight container the headspace of which is filled with the same respiration-limiting gas mixture. The seed are then be stored at 1° C. for one month. After storage, the seed are sown in soil and the rate of germination and percentage normal germinants determined.

The following gas mixtures are tested:

1. 0% oxygen, 100% nitrogen.
2. 2.5% oxygen, 97.5% nitrogen.
3. 5.0% oxygen, 95.0% nitrogen.
4. 7.5% oxygen, 92.5% nitrogen.
5. Air (i.e., atmospheric level of oxygen).
6. Control: seed prepared just prior to sowing.
7. Seed purged with 100% oxygen, then stored one month at 1° C. in air.
8. Seed purged with 100% oxygen, then stored one month at room temperature (about 20° C.) in air.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

What is claimed is:

1. A manufactured seed comprising a unit of totipotent plant tissue and a hydrated gel disposed relative to the plant tissue so as to allow liquid transfer from the gel to the plant tissue, the hydrated gel comprising a concentration of a respiration-limiting gas effective to reduce respiration of the plant tissue to a level less than respiration of totipotent plant tissue in a control manufactured seed.

2. The manufactured seed of claim 1 wherein the gas is selected from the group consisting of carbon dioxide and nitrogen.

3. The manufactured seed of claim 1 wherein the gel has an free oxygen concentration below about 10%.

4. The manufactured seed of claim 1 wherein the gel further comprises an inert oxygen-carrying compound.

5. The manufactured seed of claim 4 wherein the oxygen-carrying compound is a member of the group consisting of a perfluorocarbon and a silicone oil.

6. The manufactured seed of claim 1 further comprising a manufactured seed coat at least partially surrounding the gel and the plant tissue.

7. The manufactured seed of claim 6 wherein the seed coat comprises a gas-impermeable shell and defines an opening in the shell.

8. The manufactured seed of claim 7 wherein a gas-permeable end seal is disposed across the opening.

9. The manufactured seed of claim 7 wherein the totipotent plant tissue is sufficiently developed to comprise a radicle and the radicle is oriented toward the opening.

10. The manufactured seed of claim 1 wherein the totipotent plant tissue is sufficiently developed to comprise a shoot end, the manufactured seed further comprising a restraint enclosing at least a portion of the shoot end.

11. A method of storing a manufactured seed comprising a unit of totipotent plant tissue and a hydrated gel disposed relative to the plant tissue so as to allow liquid transfer from the gel to the plant tissue, the method comprising the steps of:

(a) exposing the manufactured seed to an atmosphere comprising a first respiration-limiting gas for a time sufficient for the gel have a concentration of the respiration-limiting gas sufficient to substantially reduce respiration of the plant tissue; then (b) storing the manufactured seed in the presence of a concentration of a second respiration-limiting gas sufficient to substantially reduce respiration of the plant tissue, thereby producing a stored seed.

12. The method of claim 11 wherein the first or second gas is selected from the group consisting of carbon dioxide and nitrogen.

13. The method of claim 11 wherein the first gas is the same as the second gas.

14. The method of claim 11 further comprising step (c) of exposing the stored seed to an atmosphere comprising molecular oxygen until the gel provides a gas environment that supports germination of the plant tissue.

15. A method of producing a manufactured seed comprising the steps of:

(a) providing a unit of totipotent plant tissue;
(b) providing a hydrated gel;
(c) disposing the plant tissue relative to the hydrated gel so as to allow liquid transfer from the gel to the plant tissue, thereby producing a manufactured seed; and
(d) exposing the hydrated gel to an atmosphere comprising a respiration-limiting gas for a time sufficient for the gel have a concentration of the respiration-limiting gas sufficient to substantially reduce respiration of the plant tissue.

16. The method of claim 15 wherein step (d) is performed after step (c).

17. A method of producing a manufactured seed comprising the steps of:

(a) providing a unit of totipotent plant tissue;
(b) disposing the plant tissue relative to a hydrated gel so as to allow liquid transfer from the gel to the plant tissue, the gel comprising a concentration of a respiration-limiting gas sufficient to substantially reduce respiration of the plant tissue, thereby producing the manufactured seed.

18. The method of claim 17 further comprising step (c) of exposing the seed to a gas environment comprising a level of molecular oxygen effective to increase respiration of the plant tissue to a level permitting germination of the plant tissue.

* * * * *